(12) United States Patent
Le Fur et al.

(10) Patent No.: US 8,697,147 B2
(45) Date of Patent: Apr. 15, 2014

(54) COSMETIC AND DERMATOLOGIC COMPOSITION AND USES THEREOF

(75) Inventors: Agnès Le Fur, Antony (FR); Carine Bezivin, Verrieres le Buisson (FR); Jean-Pierre Arnaud, Aouste sur Sye (FR); Eric Calmon, Paris (FR)

(73) Assignee: Lucas Meyer Cosmetics, Paris la Defense Cedex (FR)

( * ) Notice: Subject to any disclaimer, the term of this patent is extended or adjusted under 35 U.S.C. 154(b) by 33 days.

(21) Appl. No.: 13/428,294

(22) Filed: Mar. 23, 2012

(65) Prior Publication Data
US 2012/0245234 A1 Sep. 27, 2012

(30) Foreign Application Priority Data
Mar. 24, 2011 (FR) ...................................... 11 52445

(51) Int. Cl.
*A61K 36/18* (2006.01)
*A61K 8/00* (2006.01)
*A61K 8/73* (2006.01)

(52) U.S. Cl.
USPC .................. 424/725; 424/70.13; 424/401

(58) Field of Classification Search
USPC ....................... 424/725, 70.13, 401
See application file for complete search history.

(56) References Cited

U.S. PATENT DOCUMENTS

| | | | |
|---|---|---|---|
| 5,003,060 | A | 3/1991 | Vinot |
| 5,215,681 | A | 6/1993 | Truong et al. |
| 2008/0219937 | A1 | 9/2008 | Msika et al. |
| 2009/0041814 | A1 | 2/2009 | Nanbu |

FOREIGN PATENT DOCUMENTS

| | | |
|---|---|---|
| FR | 2600267 | 12/1987 |
| FR | 2639645 | 6/1990 |
| FR | 2889956 | 3/2007 |
| WO | WO 03/026583 | 4/2003 |
| WO | WO 2004/028501 | 4/2004 |
| WO | WO 2011/128052 | 10/2011 |

OTHER PUBLICATIONS

Database mintel, Accession No. 1128117, "Smoothing Eye Serum" Jun. 2009, pp. 1-13, XP-002664631.
Database mintel, Accession No. 1199055, "Professional Eye Serum" Oct. 2009, pp. 1-7, XP-002664632.
Database mintel, Accession No. 1341296, "Stop Cellulite Fluid" Jun. 2010, pp. 1-7, XP-002664633.

*Primary Examiner* — Gina C Justice
(74) *Attorney, Agent, or Firm* — Saliwanchik, Lloyd & Eisenschenk (57) ABSTRACT

The present invention relates to a novel natural composition comprising sclerotium gum, xanthan gum and pullulan and intended for preparing cosmetic and dermatologic compositions, to the uses thereof, and to the cosmetic and dermatologic compositions containing said novel natural composition.

22 Claims, 2 Drawing Sheets

COSMETIC AND DERMATOLOGIC COMPOSITION AND USES THEREOF

The present invention relates to the field of cosmetics and dermatology. More particularly it relates to a novel natural cosmetic and dermatologic formulation.

TECHNOLOGICAL BACKGROUND OF THE INVENTION

The natural cosmetics market is undergoing rapid change and expansion. Natural cosmetics place priority on natural resources, promote the use of ingredients derived from organic farming, preserve the environment and reduce packaging. Labels defining natural cosmetics have been developed including the Ecocert certification body in France and BDIH in Germany. In particular, to be considered a natural cosmetic, the composition must not contain unauthorized or prohibited starting materials and must comply with a series of specifications.

In this context, formulators are setting out to develop formulations having the same sensory characteristics and effectiveness as the so-called conventional formulations while having access to a much more limited number of ingredients.

One of the main problems encountered relates to the consistency of the developed formulations. In fact, many existing conventional thickeners can produce a wide range of viscosities and textures. These conventional thickeners include in particular the aqueous phase thickeners such as carbopols (carbocypolymethylene), taurate copolymers and acrylamides (non-limiting list), which give high viscosities using low thickener concentrations. The developed formulations are thus viscous and not runny. Conventional thickeners of the type such as silicone or acrylate are not authorized for use in natural cosmetics.

Natural aqueous phase thickeners are not as numerous and generally belong to the gum family: guar gum, carob gum, konjac gum, xanthan gum, sclerotium gum, acacia gum, cellulose gum (modified or not). From a chemical standpoint, they are polysaccharides obtained either by extraction from the plant (guar, carob, konjac, acacia, etc.), or by biotechnological synthesis followed by extraction (xanthan and sclerotium). Polysaccharides are macromolecules composed of chains of sugar monomer units. A macromolecule is composed of several hundred, or even several thousand, sugar residues. They differ in terms of their chemical nature.

In cosmetics, the most interesting texturizers are those which thicken and/or stabilize formulations. The thickening function occurs when the large size of the molecules "clutters" the medium, causing the molecules to get tangled up and hindering the movement of water. The gelling function occurs when the junctions between molecules create a three-dimensional space which traps water. Stabilization occurs when thickening or gelling prevents separation of the phases.

Xanthan gum is obtained by the fermentation of a hydrocarbon substrate by the *Xanthomonas campestris* bacterium. Xanthan gum is commonly used in pharmaceuticals, cosmetics and foods (additive E415) and is the object of many patents, in particular JP 2008201806 and US 2008131469 (A1). Xanthan gum is a polysaccharide with a very high molecular weight. The backbone is formed of D-glucose units to which side chains are attached, one side chain for two glucose residues. The side chain is formed of three sugars: $\alpha$-D mannose, $\beta$-glucuronic acid and a terminal $\alpha$-D mannose. Xanthan gum is known to be compatible with other hydrocolloids and in particular to form gels by synergy with galactomannans (derived for example from guar or carob). The gels have little interest in cosmetics because they often have a poor skin feel when used by the final consumer.

In the same manner, sclerotium gum is obtained by a fermentation process of the filamentous fungus *Sclerotium rolfssii* on a glucose-based medium. Some uses of sclerotium gum in cosmetics have previously been described in patent applications, in particular WO 2004028501 (A1) and JP 2004075596 (A). It is a very high molecular weight homopolysaccharide which gives only glucose residues on hydrolysis. The backbone is formed of $\beta$-D glucose residues connected by $\beta$ (1-3) glycosidic bonds with one $\beta$ (1-6)-D-glucose side chain every three glucose residues, which prevents chain aggregation.

These two products are widely used, alone or in combination, to develop both natural and conventional cosmetic formulations. They allow the production of stable, thickened solutions over a wide pH range and compatible with electrolytes. However, the concentrations of thickeners needed to obtain viscosities high enough to describe the resulting products as creams result in a runny, tacky feel which is unpleasant for the consumer. Furthermore, the suspending properties of these thickeners do not allow sufficient stabilization of an oil phase to describe the final product as a gel-cream.

Moreover, natural formulations contain many natural emollients or of natural origin such as vegetable oils (sweet almond, sunflower, grape, apricot, etc.) or vegetable butters (shea, mango, cocoa, coconut, cupuacu, illipe, etc.) which penetrate slowly after application, a characteristic which formulators consider undesirable. Solutions of xanthan and/or sclerotium gum have good spreadability but penetrate slowly and leave a greasy feel at the skin surface.

Formulators are therefore at a loss to develop natural gel-creams with a pleasant, non-greasy feel.

Pullulan is a polysaccharide obtained by biotechnology (*Aureobasidium pullulans*) from starch. It is used to form edible films (food additive E1204). The backbone is a linear a-glucan chain formed of three glucose residues linked $\alpha$-(1-4) in maltotriose units which are connected to each other by $\alpha$-(1-6) glycosidic bonds. The structure can contain up to 10% maltotetraose and $\alpha$-(1-3) branch linkages. Depending on the methods of biosynthesis and purification, pullulan can contain heteropolysaccharides and acid polysaccharides as impurities. In aqueous solution it has low viscosity (hence it cannot be described as a thickener); a 2% aqueous solution of pullulan has an apparent viscosity of approximately 2-3.5 mPa·s. Its adhesive properties together with its good water solubility are what allow its use for developing breath freshener films. On the other hand, these properties are of little interest in cosmetics because tackiness is a negative feature that formulators try to eliminate from their formulations. In addition, the absence of thickening properties makes it of no use to adjust viscosity. Finally, its film-forming ability tends to result in the formation of "fluff" when applied. Nonetheless the film-forming properties of pullulan have been used in cosmetics to form visible films at the skin surface (WO 03026583 (A3)).

Fructan is a polysaccharide obtained by biotechnology whose properties of adhesion and in aqueous solution are very similar to those of pullulan. However, its chemical composition is different: it is a chain of $\beta$-(2-6) fructose units with $\beta$-(2-1) branches. Like pullulan, it is not a thickener and it forms tacky films.

SUMMARY OF THE INVENTION

In a sensory study, it was discovered, in a surprising manner, that the addition of pullulan to a mixture of sclerotium and xanthan gums led to a reduction in a greasy feel, without lowering viscosity or increasing tackiness. The resultant thickened solution was cool, not runny, easy to spread, penetrated rapidly, did not form a film and met the criteria of a natural cosmetic. Furthermore, although it is similar to fructan, in an equally surprising manner its sensory effect in association with xanthan gum and sclerotium gum was distinctly different.

The present invention therefore relates to a composition intended for preparing a cosmetic or dermatologic composition, in particular a natural composition, comprising at least the association of sclerotium gum, xanthan gum and pullulan.

Preferably, said composition comprises, based on the total weight of the association of sclerotium gum, xanthan gum and pullulan: 40-85% by weight of sclerotium gum; 10-50% by weight of xanthan gum; and 5-30% by weight of pullulan, the sum of the percentages being equal to 100%. In a preferred embodiment, said composition comprises, based on the total weight of the association of sclerotium gum, xanthan gum and pullulan: 40-70% by weight of sclerotium gum; 15-45% by weight of xanthan gum; and 10-30% by weight of pullulan, the sum of the percentages being equal to 100%. In a more particular embodiment, said composition comprises, based on the total weight of the association of sclerotium gum, xanthan gum and pullulan: approximately 50% by weight of sclerotium gum; approximately 30% by weight of xanthan gum; and approximately 20% by weight of pullulan, the sum of the percentages being equal to 100%.

Preferably, the association of sclerotium gum, xanthan gum and pullulan accounts for at least 30% by weight of the total weight of the composition, preferably between 30 and 80%, even more preferably between 50 and 80%.

In a preferred embodiment, the composition additionally comprises phospholipids and/or lysophospholipids, preferably lecithin and/or lysolecithin, even more preferably unsaturated lysolecithin. In this preferred embodiment, the composition comprises, based on the total weight of the composition: 20-70% by weight of phospholipids and/or lysophospholipids, preferably lecithin and/or lysolecithin, even more preferably unsaturated lysolecithin; 20-85% by weight of sclerotium gum; 5-50% by weight of xanthan gum; and, 5-30% by weight of pullulan, the sum of the percentages not exceeding 100%. In a preferred embodiment, said composition comprises, based on the total weight of the composition: 20-50% by weight of phospholipids and/or lysophospholipids, preferably lecithin and/or unsaturated lysolecithin, even more preferably unsaturated lysolecithin; 20-45% by weight of sclerotium gum; 10-25% by weight of xanthan gum; and, 5-20% by weight of pullulan, the sum of the percentages not exceeding 100%. In a more particular embodiment, said composition comprises, relative to the total weight of the composition: approximately 40% by weight of phospholipids and/or lysophospholipids, preferably lecithin and/or unsaturated lysolecithin, even more preferably unsaturated lysolecithin; approximately 35% by weight of sclerotium gum; approximately 15% by weight of xanthan gum; and, approximately 10% by weight of pullulan. In a particularly preferred embodiment, the composition will comprise unsaturated lysolecithin.

The composition intended for preparing a cosmetic or dermatologic composition preferably takes the form of a powder, which can possibly be compressed into the form of a bar or granules.

The present invention also relates to a use of a composition described hereinabove for preparing a cosmetic or dermatologic composition.

The present invention also relates to cosmetic or dermatologic compositions comprising the composition described hereinabove. In particular, the cosmetic or dermatologic composition contains from 0.1-10% by weight of such a composition based on the total weight of the cosmetic or dermatologic composition.

Lastly the present invention relates to a method for preparing cosmetic or dermatologic compositions comprising adding a composition such as described hereinabove to the component(s) of the cosmetic or dermatologic composition and recovering the cosmetic or dermatologic composition obtained.

DETAILED DESCRIPTION OF THE INVENTION

A first object of the present invention therefore relates to the association of sclerotium gum, xanthan gum and pullulan. In particular said association is included in a composition intended for preparing a composition intended for preparing cosmetic and dermatologic compositions, thereby conferring a thickening effect pleasant to the touch. It thus constitutes a natural thickening-emulsifying composition. It is therefore quite particularly suited to preparing a natural cosmetic or dermatologic composition. However, it possesses such qualities that it is not limited to this use. In fact, more generally, the composition according to the invention is a composition with a thickening-emulsifying property and it can also be used for preparing a cosmetic or dermatologic composition with a natural image (that is to say, tending to be natural but not meeting the standards to obtain the natural label), or even conventional.

Typically, in the composition according to the invention, these three components can be present in the following proportions:
approximately 40-85% by weight of sclerotium gum;
approximately 10-50% by weight of xanthan gum; and
approximately 5-30% by weight of pullulan,
the sum of the percentages being equal to 100%, and the percentages being based on the total weight of the association of sclerotium gum, xanthan gum and pullulan.

In the present application, the term "approximately" is understood to mean a variation of plus or minus 10% of the value, preferably plus or minus 5% of the value. For example, for a value of 20, "approximately 20" is understood to mean between 18-22 when one considers a variation of 10% and 19-21 when one considers a variation of 5%.

In a preferred embodiment, the three components are present in the following proportions: approximately 40-70% by weight of sclerotium gum; approximately 15-45% by weight of xanthan gum; and approximately 10-30% by weight of pullulan, the sum of the percentages being equal to 100%.

In a more particular embodiment, this composition comprises, based on the total weight of the association of sclerotium gum, xanthan gum and pullulan: approximately 50% by weight of sclerotium gum; approximately 30% by weight of xanthan gum; and approximately 20% by weight of pullulan, the sum of the percentages being equal to 100%.

Preferably, the association of sclerotium gum, xanthan gum and pullulan accounts for at least 30% by weight of the total weight of the composition, preferably between 30 and 80%, even more preferably between 50 and 80%.

Said composition is manufactured by mixing the different ingredients with the aid of appropriate equipment (for example, a coulter, blade, turning mixer). Said composition is preferably prepared in the form of a powder. Where necessary, the power obtained can be sterilized (in particular, rid of bacteria) by suitable methods such as irradiation or high pressure. If desired, the powder can be compacted by classical methods well known to one of skill in the art. For instance, the powder can be compacted into bars or granules.

Pullulan is a polysaccharide obtained by the fermentation of starch by *Aureobasidium pullulans*. Pullulan is produced for example under the reference Pullulan PF 20 by the Hayashibara group in Japan, or else under the name Pullulan by Sigma-Aldrich.

Xanthan gum is obtained by the fermentation of a hydrocarbon substrate by the *Xanthomonas campestris* bacterium. The resulting mixture is purified with alcohol (ethanol or isopropanol), pressed, dried and milled. The resulting powder can optionally be sterilized by irradiation or high pressure. Xanthan gum is commonly used in pharmaceuticals, cosmetics and foods (additive E415) and is the object of many patents. Xanthan gum is a very high molecular weight polysaccharide. The backbone is formed of D-glucose units to which side chain are attached, one side chain for two glucose residues. The side chain is composed of three sugars: $\alpha$-D mannose, $\beta$-glucuronic acid and a terminal $\alpha$-D mannose. Xanthan gum is commercially available and in particular is marketed under the names KELTROL, KELTROL T, KELTROL TF, KELTROL BT, KELTROL CG-BT, KELTROL RD, KELTROL CG by NUTRASWEET KELCO, or under the names RHODICARE S, RHODICARE H, RHODICARE XC by RHODIA CHIMIE, or under the name Satiaxane CX 91 by the Cargill Group, or under the name Rheocare XG by BASF. Xanthan gum can also be modified to facilitate its use. This type of gum (INCI name=dehydroxanthan gum) is marketed under the reference Amaze XT by Akzo Nobel. Other modified xanthan gums exist and can eventually be obtained, in particular by enzymatic treatments or by using modified strains. However, in a preferred embodiment, the xanthan gum is not modified.

Sclerotium gum is obtained by fermentation of a glucose-based substrate by the filamentous fungus *Sclerotium rolfssii*. The resulting mixture is purified with alcohol (ethanol or isopropanol), pressed, dried and milled. The resulting powder can optionally be sterilized by irradiation or high pressure. Sclerotium gum is a very high molecular weight homopolysaccharide which gives only glucoses after hydrolysis. The backbone is composed of $\beta$-D glucose residues connected by $\beta$ (1-3) glycosidic bonds with one $\beta$ (1-6)-D-glucose side chain every three glucose residues, which prevents chain aggregation. Sclerotium gum is also called sclerote gum(s) or scleroglucan gum or scleroglucan. Sclerotium gum is commercially available and in particular is marketed under the name ACTIGUM CS by SANOFI BIO INDUSTRIES, and in particular ACTIGUM CS 11, and under the name AMIGEL and AMIGUM by ALBAN MULLER INTERNATIONAL, or else under the name Tinoderm SG-L by BASF. This sclerotium gum can eventually be modified, in particular by enzymatic treatments or by using modified strains. However, in a preferred embodiment, the sclerotium gum is not modified.

The composition comprising the association of sclerotium gum, xanthan gum and pullulan provides for the preparation of cosmetic or dermatologic compositions in the form of thickened solutions.

However, the natural thickening-emulsifying composition according to the invention can additionally comprise one or more phospholipids and/or lysophospholipids.

Lecithin is defined as a mixture of polar and neutral lipids containing at least 60% polar lipids. By polar lipids, one should understand in particular phospholipids and glycolipids. Phospholipids are natural amphipilic compounds. They are naturally present in soy, sunflower, maize, rice, eggs, milk, and fish oil. Lecithin is obtained by degumming phospholipid-rich oil. It can then be purified or modified. Known methods of purification are for example extraction with acetone or ethanol or chromatography. Methods of modification are for example acetylation, hydroxylation or else enzymatic hydrolysis. Some phospholipids are composed of a glycerol backbone to which one or two fatty acids are attached (apolar part of the phospholipid) as well as a phosphate group. It is the phosphate group substituent (polar part of the phospholipid) that determines the phospholipid nomenclature (phosphatidylcholine, phosphatidylethanolamine, phosphatidylinositol, phosphatidic acid, phosphatidylserine, etc.). Hydrogenation is the process of saturating the double bonds present in the molecule. The resulting product is less susceptible to oxidative phenomena and has a higher melting point. The final hydrophilic/lipophilic balance (HLB) of the molecule is decreased. Enzymatic hydrolysis is the process of breaking the bond between the glucose backbone and one or two fatty acids. The resulting molecule is smaller and its hydrophilic/lipophilic balance (HLB) is higher. By their amphipilic structure, phospholipids can therefore modify the tension between the aqueous phase/organic phase interface, without for all that being on the list of cosmetic emulsifiers. Their association with the composition described hereinabove provides viscous gel-creams with a sophisticated feel.

The selected phospholipids can be unsaturated and/or hydrogenated and/or hydrolyzed. In a preferred embodiment of the present invention, the use of unsaturated lysophospholipids allows development of a formulation by cold processing and maximally reduces the size of oil droplets in suspension in the thickened solution, thereby optimizing the stability of the formulation.

Thus, the composition according to the invention additionally comprises one or more phospholipids and/or lysophospholipids.

Preferred phospholipids and/or lysophospholipids are lecithin. Lecithin can be used in hydrogenated form or not, preferably unsaturated. Lecithin can also be in the form of lysolecithin. In the preferred embodiment of the invention, the composition contains unsaturated lysolecithin. It can comprise unsaturated lysolecithin in purified form or in the form of a mixture with other phospholipids and/or lysophospholipids, in particular lecithin.

Lecithin can be obtained from various sources, particularly soy, sunflower, milk, eggs, rice, maize, and the like. It is commercially available, for example under the reference Solec SF 10 from The Solae Company, or else under the reference Emulmetik 300 from Lucas Meyer Cosmetics. Many other grades of lecithin are available from Solec, Lucas Meyer Cosmetics, Cargill, Natterman, or Lipoid. Lecithins are typically obtained from oil which can be extracted from seeds by pressing or with the aid of suitable solvents. Once the oil is obtained, lecithin is extracted for example by degumming the oil. It can then be filtered. Advantageously lecithin contains at least 60% polar lipids insoluble in acetone. It contains different phospholipids including phosphatidylcholine, phosphatidylethanolamine, phosphatidylinositol and phosphatidic acid. Hydrogenated lecithin can be obtained from different methods known per se. For instance, according to one method that can be used, lecithin is dissolved in a solvent system then hydrogenated for 1 to 20 hours under 10 to 200 kg/cm$^2$ of hydrogen pressure at a temperature of 50-90° C. in the presence of a catalyst. Hydrogenation improves lecithin stability, in particular with regard to oxidation or other degradations. These hydrogenated lecithins are available from Lucas Meyer Cosmetics under the references Emulmetik 320, Emulmetik 950 (non-exhaustive list). Other hydrogenated lecithins are available from Natterman or Lipoid.

With regard to lysolecithin, it can be obtained for example by enzymatic hydrolysis of phospholipids, thereby leading to the elimination of one or two fatty acid chains. These methods are well known to one of skill in the art (see introduction in US2007009644). Lysolecithin is also commercially available, in particular under the name SLP-LPC70 from Tsuji Oil Mill Co., Ltd. and under the name Lysolecithin Kyowa from Kyowa Hakko Kogyo Co., Ltd, or else under the names Emulmetik 120, Emulmetik 350 and Emulmetik 355 from Lucas Meyer Cosmetics.

Thus, the composition of the present invention, intended for preparing cosmetic or dermatologic compositions, preferably comprises the association of sclerotium gum, xanthan gum, pullulan and phospholipids and/or lysophospholipids. Preferably, the phospholipids and/or lysophospholipids will be a lecithin and/or a lysolecithin, preferably unsaturated and/or hydrogenated and/or hydrolyzed, even more preferably unsaturated. In an especially preferred embodiment, the composition comprises unsaturated lysolecithin.

More specifically, the composition comprises, based on the total weight of the composition: 20-70% by weight of phospholipids and/or lysophospholipids, preferably lecithin and/or lysolecithin, even more preferably unsaturated lysolecithin; 20-85% by weight of sclerotium gum; 5-50% by weight of xanthan gum; and, 5-30% by weight of pullulan, the sum of the percentages not exceeding 100%. In a preferred embodiment, this composition comprises, based on the total weight of the composition: 20-50% by weight of phospholipids and/or lysophospholipids, preferably lecithin and/or lysolecithin, even more preferably unsaturated lysolecithin; 20-45% by weight of sclerotium gum; 10-25% by weight of xanthan gum; and, 5-20% by weight of pullulan, the sum of the percentages not exceeding 100%. In a more particular embodiment, this composition comprises, based on the total weight of the composition: approximately 40% by weight of phospholipids and/or lysophospholipids, preferably lecithin and/or lysolecithin, even more preferably unsaturated lysolecithin; approximately 35% by weight of sclerotium gum; approximately 15% by weight of xanthan gum; and, approximately 10% by weight of pullulan. In an especially preferred embodiment, the composition will comprise unsaturated lysolecithin.

Preferably, the association of sclerotium gum, xanthan gum, pullulan and phospholipids and/or lysophospholipids accounts for at least 50% by weight of the total weight of the composition (preferably, at least 60, 70, 80, 90 or 95%), even more preferably between 80 and 100%.

Said composition can easily be produced by mixing the ingredients with the aid of appropriate equipment (for example, a coulter, blade, turning mixer). Said composition is preferably prepared in the form of a powder. Where necessary, it can be sterilized (and in particular, rid of bacteria) by suitable methods known to one of skill in the art such as for example irradiation or high pressure. If desired, the powder can be compacted by classical methods well known to one of skill in the art. Thus, the powder can be compressed into bars or granules.

Figure 1:
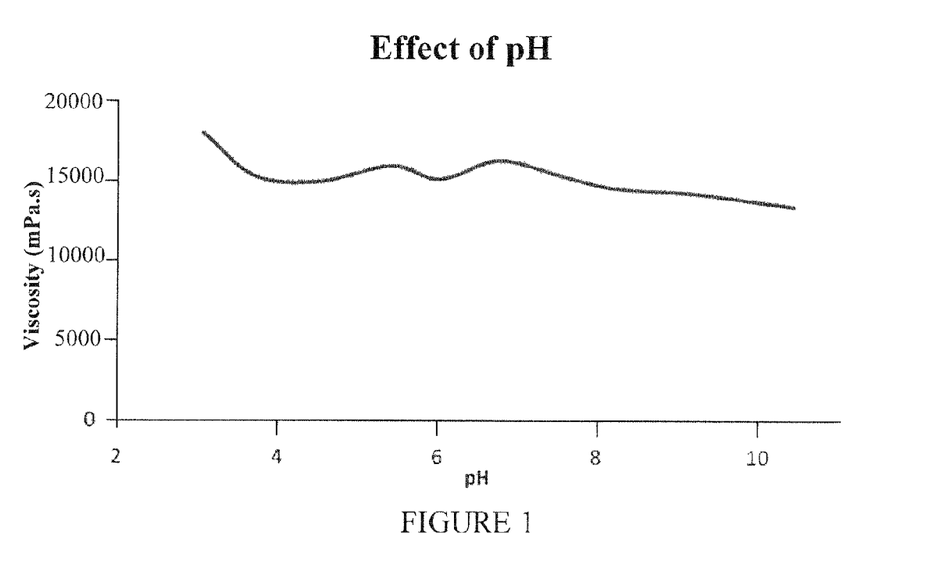
FIG. 1: Effect of pH on the viscosity of solutions containing 2% by weight of a composition according to the invention.
Figure 2:
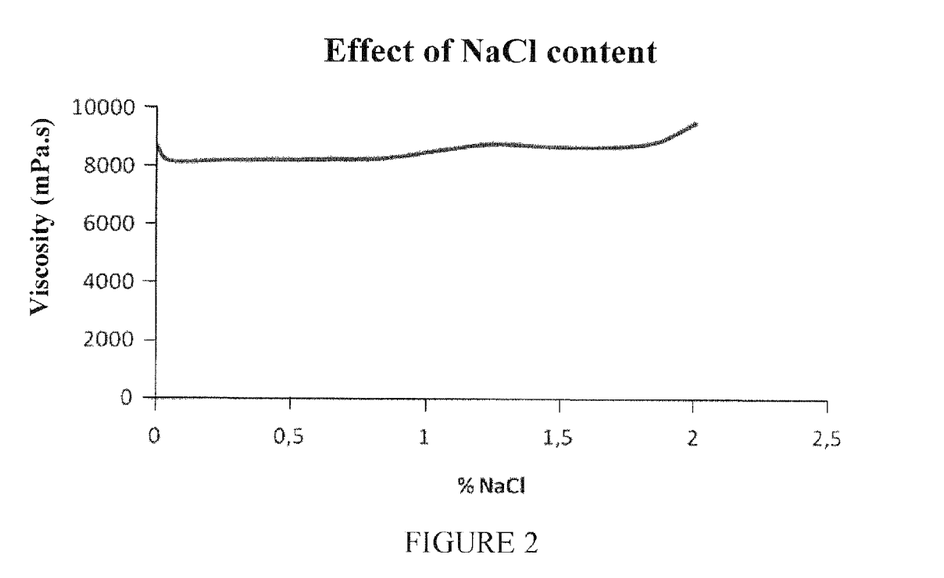
FIG. 2: Effect of NaCl content on the viscosity of solutions containing 2% by weight of a composition according to the invention.
Figure 3:
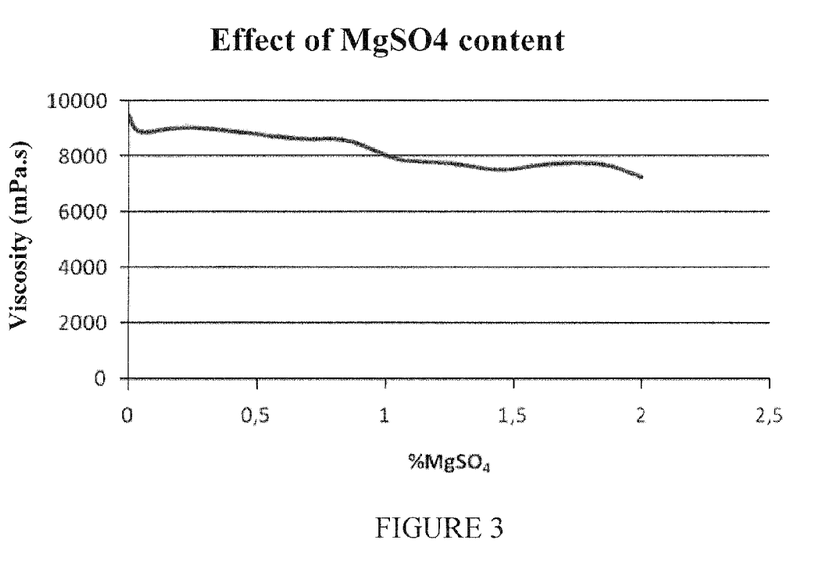
FIG. 3: Effect of $MgSO_4$ content on the viscosity of solutions containing 2% by weight of a composition according to the invention.

The composition according to the invention has the following characteristics. It preferably takes the form of a beige, weakly odorous powder. Dispersed in water according to a classical method, it produces thick, opalescent beige solutions. Temperature, UV, shear, presence of electrolytes or pH variations have little effect on the viscosities of the solutions thus formed (FIGS. 1-3).

The thickened solutions (also called gels in the present document) are compatible with any type of emollient, preservatives, pigments, vitamins, active agents, emulsifiers, UV filters and sunscreens, surfactants, thermal water, flower water, liposomes or other vectorization systems, cyclodextrin, perfume, humectants, glycols, vegetable oils, vegetable butters, natural or synthetic waxes, silicones, chelating agents, antioxidants, sugars. They allow the development of formulations intended for application on the skin, hair or nails. In a particular embodiment, all the components of the composition meet the standards defining natural cosmetics, in particular the Ecocert and BDIH labels. In another embodiment, the composition can comprise any component compatible with a cosmetic or dermatologic composition. In particular, the composition according to the present invention can comprise one or more active ingredients. In particular, active ingredients satisfying the natural label standards are preferred and in particular those from renewable resources and meeting the requirements of sustainable development.

These formulations can be lotions, milks, creams, water-in-oil or oil-in-water emulsions, multiple emulsions, sprays, gels, gel-creams, suspensions, cleansing products, make-up products, hair dyes, hair styling products, hair care products, i.e., any type of cosmetic product (non-limiting list). They are also compatible and can be used with other natural or synthetic thickeners.

Thus, the present invention relates to the use of a natural thickening-emulsifying composition according to the present invention for preparing a cosmetic and dermatologic composition and to the cosmetic and dermatologic composition so obtained. The present invention relates to a cosmetic or dermatologic composition comprising the natural thickening-emulsifying composition according to the present invention. In particular, said cosmetic or dermatologic composition contains from 0.1 to 10% by weight of a natural thickening-emulsifying composition according to the present invention based on the total weight of the composition. Preferably, it contains from 0.2 to 5% by weight thereof. In a particular embodiment, it contains 0.5 to 2% by weight thereof. Thanks to the excellent stability of the viscosity of the compositions prepared with the aid of the natural thickening-emulsifying composition according to the present invention (particularly with respect to pH, temperature and electrolyte concentrations), the cosmetic or dermatologic compositions according to the present invention can have a pH comprised between pH 2 and pH 13. Moreover, the cosmetic or dermatologic compositions according to the present invention can comprise electrolytes, in particular up to 2% by weight of electrolytes. These cosmetic or dermatologic compositions can comprise any component of cosmetic or dermatologic compositions. Non-limiting examples include emollients, preservatives, pigments, vitamins, active agents, emulsifiers, UV filters and sunscreens, surfactants, thermal water, flower water, liposomes or other vectorization systems, cyclodextrins, electrolytes, pH adjusters, perfumes, humectants, glycols, vegetable oils, vegetable butters, natural or synthetic waxes, silicones, chelating agents, antioxidants, and sugars. Thus, said cosmetic compositions can be intended for application on the skin, hair or nails. They can take the form of lotions, milks, creams, water-in-oil or oil-in-water emulsions, multiple emulsions, sprays, gels, gel-creams, suspensions, viscous solutions, cleansing products, make-up products, hair dyes, hair styling products, hair care products (non-limiting list).

In particular, the present invention relates to a cosmetic method comprising applying the cosmetic composition according to the present invention on the skin, hair or nails.

The present invention also relates to a method for preparing a cosmetic or dermatologic composition comprising a step of mixing the natural thickening-emulsifying composition according to the present invention with some of or the components of the cosmetic or dermatologic composition and recovering said components. The composition according to the invention will preferably be added to the hot aqueous phase (temperature greater than or equal to 65° C.) with mechanical stirring and maintained under mechanical stirring for a sufficient time (the time depends on the type of stirrer used and the stirring speed) to form the gel. Any type of stirrer can be used, in particular helices, deflocculants, centripetal stirrers, rotor-stator or ultrasound, high pressure homogenizers (list non-limiting). The remainder of the manufacture takes place according to classical methods known to one of skill in the art for the manufacture of gels, emulsions, gel-creams, viscous solutions, and the like. The compositions according to the invention can also be used at room temperature.

The advantages of the present invention will become clearer in the following examples.

EXAMPLES

Example 1

Sensory Study No. 1

Sensory testing was carried out under conditions conforming to V09-105 norms.

Twelve experts each evaluated three products during the same session using preestablished product-references and scales, in individual, independent tests.

The scale comprised values from 0 to 10. The value 0 corresponds to the absence of this descriptor in the product. The value 10 corresponds to the maximum value of this descriptor in the product.

In addition to the composition such as described in the table at 1% (by weight), the test products comprised 0.5% Dekaben C (preservative) and purified water (QSP 100%).

Furthermore, the composition (added at 1%) contained

35% sclerotium gum

15% xanthan gum

50% lecithin and optionally 10% pullulan or fructan.

Each panelist entered his results which were then analyzed to determine if there was a difference between products with regard to the parameters tested. These results are presented in the following table.

| Composition at 1% | Test No. | | | Differences |
|---|---|---|---|---|
| | 1 | 2 | 3 | |
| | Sclerotium gum + xanthan gum + lecithin | | | |
| | pullulan | — | fructan | |
| Parameter: Fluid | 8.05 | 8.33 | 8.05 | No difference between tests |
| Parameter: Runny | 3.71 | 3.48 | 3.57 | No difference between tests |
| Parameter: Film-forming | 0.38 | 0.33 | 0.38 | No difference between tests |
| Parameter: Greasy | 4.00 | 4.57 | 4.76 | Test 1 less greasy than tests 2 and 3 |
| Parameter: Penetrating | 6.14 | 6.29 | 5.43 | Tests 1 and 2 more penetrating than test 3 |

Example 2

Sensory Study No. 2

Sensory testing was carried out under conditions conforming to V09-105 norms.

Twenty experts each evaluated two products during the same session using preestablished product-references and scales, in individual, independent tests.

The scale comprised values from 0 to 10. The value 0 corresponds to the absence of this descriptor in the product. The value 10 corresponds to the maximum value of this descriptor in the product Each panelist entered his results which were then analyzed to determine if there was a difference between products with regard to the parameters tested. These results are presented in the following table.

| Composition | Test No. | | Difference |
|---|---|---|---|
| | 4 Water Composition as per example 1 at 1% 0.5% Dekaben C | 5 Water 0.15% Carbopol ETD 2020 0.5% Dekaben C NaOH qsp pH 5.5 | |
| Shiny | 6.10 | 6.60 | No difference between tests |
| Slippery | 8.35 | 7.35 | No difference between tests |
| Whitening | 0.00 | 0.00 | No difference between tests |
| Spreadability | 8.80 | 8.75 | No difference between tests |
| Tackiness | 2.50 | 1.30 | No difference between tests |
| Soft | 4.40 | 4.35 | No difference between tests |
| Penetrating | 7.75 | 8.20 | No difference between tests |
| Film-forming | 1.10 | 0.50 | No difference between tests |

Example 3

Effect of pH and Electrolytes on Viscosity

FIGS. 1-3 illustrate the effect of variations in pH or addition of mono- or divalent electrolytes on solutions containing 2% of a composition such as described in example 1. Viscosity was measured at room temperature with a viscometer (Rheo ELV8, spindle 4, 6 rpm, 3 minutes). pH and addition of mono- or divalent electrolytes had little effect on the viscosity of the solutions.

Example 4

Composition and Preparation of a Lifting Eye Contour

| PHASE | INGREDIENT (Trade names) | INCI NAME | Supplier | % (w/w) |
|---|---|---|---|---|
| A | Deionized water | Water | — | 90.40 |
|   | Dermofeel ™ PA3 | Sodium phytate (and) Water | Dr Straetmans GmbH | 0.10 |
|   | Granlux ™ AOX GL | Glycerin (and) *Picea abies* extract (and) Alcohol | Granula Oy | 1.00 |
| B | Composition according to example 1 | Lysolecithin (and) Sclerotium gum (and) Xanthan gum (and) Pullulan | Lucas Meyer Cosmetics | 1.00 |
| C | Riboxyl ™ | Ribose | Lucas Meyer Cosmetics | 0.50 |
|   | Deionized water | Water | — | 1.00 |
| D | Liftessence ™ Nature PF | Water (and) Glycerin (and) *Cyathea cumingii* leaf extract | Lucas Meyer Cosmetics | 2.00 |
| E | Dermosoft ™ 1388 eco | Fragrance | Dr Straetmans GmbH | 4.00 |

Operating Method:
1—Heat A at 65-75° C.
2—Sprinkle B while stirring and continue stirring for at least 20 minutes.
3—Homogenize.
4—Cool under stirring.
5—Add C, D and E at a temperature below 40° C.
6—Adjust the pH if necessary.

Example 5

Composition and Preparation of a Moisturizing Gel-Cream

| PHASE | INGREDIENT (Trade names) | INCI NAME | Supplier | % (w/w) |
|---|---|---|---|---|
| A | Mineral water | Water | — | 77.50 |
|   | Dermofeel ™ PA3 | Sodium phytate (and) Water | Dr Straetmans GmbH | 0.10 |
| A' | Composition according to example 1 | Lysolecithin (and) Sclerotium gum (and) Xanthan gum (and) Pullulan | Lucas Meyer Cosmetics | 2.00 |
| B | Sweet almond oil | *Prunus amygdalus dulcis* (sweet almond) oil | Jan dekker | 3.00 |
|   | Shea butter | *Butyrospermum parkii* (Shea) butter | Sictia | 4.00 |
|   | Dermofeel ™ Sensolv | Isoamyl laurate | Dr Straetmans GmbH | 2.00 |
|   | Dermofeel ™ Toco 70 | Tocopherol | Dr Straetmans GmbH | 0.20 |
| C | Dermosoft ™ 1388 eco | Fragrance | Dr Straetmans GmbH | 4.00 |
| D | Sculptessence ™ | Water (and) Glycerin (and) *Linum usitatissimum* (linseed) seed extract | Lucas Meyer Cosmetics | 5.00 |
|   | Suprem' ™ nature coton | Water (and) *Helianthus annuus* (Sunflower) seed oil (and) Lecithin (and) Polyglyceryl-3 diisostearate (and) Glycerin (and) Glyceryl stearate (and) *Gossypium herbaceum* (Cotton) extract | Lucas Meyer Cosmetics | 2.00 |
| E | Douceur 3246 | Fragrance | Vanessence | 0.20 |

Operating Method:
1—Heat A and B at 65-75° C.
2—Sprinkle A' in A under mechanical stirring.
3—Continue stirring for at least 20 minutes.
4—Add B.
5—Homogenize.
6—Cool.
7—Add D and E at a temperature below 40° C.
8—Adjust the pH if necessary.

Example 6

Composition and Preparation of an Anti-Age Emulsion

| PHASE | INGREDIENT (Trade names) | INCI NAME | Supplier | % (w/w) |
|---|---|---|---|---|
| A | Deionized water | Water | — | 62.90 |
|  | Biophilic ™ H | Hydrogenated lecithin (and) C12-16 alcohols (and) Palmitic acid | Lucas Meyer Cosmetics | 4.00 |
|  | Chlorphenesin | Chlorphenesin | Interchimie | 0.30 |
|  | Dermofeel ™ PA3 | Sodium phytate (and) Water | Dr Straetmans GmbH | 0.10 |
| A' | Composition according to example 1 | Lysolecithin (and) Sclerotium gum (and) Xanthan gum (and) Pullulan | Lucas Meyer Cosmetics | 1.00 |
| B | Dermofeel ™ GSC | Glyceryl stearate citrate | Dr Straetmans GmbH | 1.00 |
|  | Dermofeel ™ BGC | Butylene glycol dicaprylate/dicaprate | Dr Straetmans GmbH | 8.00 |
|  | Shea butter | *Butyrospermum parkii* (Shea) butter | Sictia | 3.00 |
|  | Cegesoft PS6 | Vegetable oil (Olus) | BASF | 3.00 |
|  | Dermofeel ™ Sensolv | Isoamyl laurate | Dr Straetmans GmbH | 3.00 |
|  | Dermofeel ™ toco 70 | Tocopherol | Dr Straetmans GmbH | 0.20 |
|  | DC 200,50 cs | Dimethicone | Dow Corning | 0.30 |
|  | Cetiol C5 | Coco-caprylate | BASF | 3.00 |
| C | Mamaku vital essence nature PF | Water (and) Glycerin (and) *Cyathea medullaris* leaf extract | Lucas Meyer Cosmetics | 2.00 |
|  | Sculptessence ™ | Water (and) Glycerin (and) *Linum usitatissimum* (linseed) seed extract | Lucas Meyer Cosmetics | 5.00 |
| D | Dermosoft ™ 1388 | Fragrance | Dr Straetmans GmbH | 3.00 |
| E | Douceur 3246 | Fragrance | Vanessence | 0.20 |

Operating Method:
1—Heat A and B at 75-85° C.
2—Sprinkle A' in A under mechanical stirring.
3—Continue stirring for at least 20 minutes.
4—Add B.
5—Homogenize.
6—Cool.
7—Add C, D and E at a temperature below 40° C.

Example 7

Composition and Preparation of a Nourishing Shampoo

| PHASE | INGREDIENT (Trade names) | INCI NAME | Supplier | % (w/w) |
|---|---|---|---|---|
| A | Deionized water | Water | — | 66.95 |
|  | Dermofeel ™ PA3 | Sodium phytate (and) Water | Dr Straetmans GmbH | 0.10 |
|  | Tegobetain F50 | Cocamidopropyl betain | Evonik | 4.45 |
|  | Dermosoft ™ 1388 | Fragrance | Dr Straetmans GmbH | 2.00 |
|  | Dermofeel ™ G10LW | Polyglyceryl-10 laurate (and) Water | Dr Straetmans GmbH | 2.00 |

-continued

| PHASE | INGREDIENT (Trade names) | INCI NAME | Supplier | % (w/w) |
|---|---|---|---|---|
| | Texapon N70 | Sodium laureth sulfate | BASF | 9.50 |
| | Sodium chloride | Sodium chloride | — | 2.80 |
| | 15% citric acid solution | Water (and) Citric acid | — | Up to pH 5.5 |
| B | Deionized water | Water | — | 9.50 |
| B' | Composition according to example 1 | Lysolecithin (and) Sclerotium gum (and) Xanthan gum (and) Pullulan | Lucas Meyer Cosmetics | 0.50 |
| C | Douceur 3246 | Fragrance | Vanessence | 0.20 |
| D | Suprem'™ Nature Karite | Water (and) *Butyrospermum parkii* (Shea) butter (and) lecithin (and) Polyglyceryl-3 diisostearate (and) Glycerin (and) Glyceryl stearate | Lucas Meyer Cosmetics | 2.00 |

Operating Method:
1—Successively mix the ingredients of A with slow stirring.
2—Prepare B=sprinkle B' in B preheated to 65-75° C. Continue stirring for at least 20 minutes. Homogenize.
3—Add B (hot or cold) to A.
4—Add C and D.
5—Adjust the pH if necessary.

We claim:

1. A composition comprising a combination of sclerotium gum, xanthan gum and pullulan and wherein:
   sclerotium gum accounts for 40-85% by weight of the total weight of the combination of sclerotium gum, xanthan gum and pullulan,
   xanthan gum accounts for 10-50% by weight of the total weight of the combination of sclerotium gum, xanthan gum and pullulan, and
   pullulan accounts for 5-30% by weight of the total weight of the combination of sclerotium gum, xanthan gum and pullulan
   the sum of the percentages for the combination of sclerotium gum, xanthan gum and pullulan being equal to 100%.

2. The composition according to claim 1, wherein the combination of sclerotium gum, xanthan gum and pullulan provides at least 30% of the composition by weight.

3. The composition according to claim 1, additionally comprising phospholipids and/or lysophospholipids.

4. The composition according to claim 3, wherein the phospholipids and/or lysophospholipids are lecithin and/or lysolecithin.

5. The composition according to claim 3, comprising
   20-70% by weight of phospholipids and/or lysophospholipids;
   20-85% by weight of sclerotium gum;
   5-50% by weight of xanthan gum; and
   5-30% by weight of pullulan;
   the percentages being expressed based on the total weight of said composition and the sum of the percentages not exceeding 100%.

6. The composition according to claim 5, comprising
   20-50% by weight of phospholipids and/or lysophospholipids;
   20-45% by weight of sclerotium gum;
   10-25% by weight of xanthan gum; and
   5-20% by weight of pullulan;
   the percentages being expressed based on the total weight of said composition and the sum of the percentages not exceeding 100%.

7. The composition according to claim 1 in the form of a powder, optionally compressed into bars or granules.

8. The composition according to claim 2, wherein the combination of sclerotium gum, xanthan gum and pullulan provides for about 30 to 80% of said composition by weight.

9. The composition according to claim 4, wherein the phospholipids and/or lysophospholipids are unsaturated lysolecithin.

10. The composition according to claim 5, wherein the phospholipids and/or lysophospholipids are lecithin and/or lysolecithin.

11. The composition according to claim 5, wherein the phospholipids and/or lysophospholipids are unsaturated lysolecithin.

12. The composition according to claim 6, wherein the phospholipids and/or lysophospholipids are lecithin and/or lysolecithin.

13. The composition according to claim 6, wherein the phospholipids and/or lysophospholipids are unsaturated lysolecithin.

14. The composition of claim 1 which further comprises a compound selected from a phospholipid, a lysophospholipid and combinations thereof.

15. The composition of claim 1, wherein the combination of sclerotium gum, xanthan gum and pullulan provide from 50% to 80% of the composition by weight.

16. A cosmetic or dermatologic composition comprising:
   a cosmetic or dermatologic component, and
   a combination of sclerotium gum, xanthan gum and pullulan wherein:
      sclerotium gum accounts for 40-85% by weight of the total weight of the combination of sclerotium gum, xanthan gum and pullulan,
      xanthan gum accounts for 10-50% by weight of the total weight of the combination of sclerotium gum, xanthan gum and pullulan, and
      pullulan accounts for 5-30% by weight of the total weight of the combination of sclerotium gum, xanthan gum and pullulan
      the sum of the percentages of sclerotium gum, xanthan gum and pullulan being equal to 100%.

17. The cosmetic or dermatologic composition according to claim 16, wherein the combination of sclerotium gum, xanthan gum and pullulan provides for 0.1 to 10% by weight of the total weight of said cosmetic or dermatologic composition.

18. The cosmetic or dermatologic composition according to claim 16, said cosmetic or dermatologic composition further comprising a compound selected from a phospholipid, a lysophospholipid and combinations thereof.

19. The cosmetic or dermatologic composition according to claim 18, wherein the combination of sclerotium gum, xanthan gum, pullulan, phospholipids and/or lysophospholipids provides for 0.1% to 10% of the total weight of said composition.

20. The cosmetic or dermatologic composition according to claim 16, wherein the cosmetic or dermatologic component comprises an emollient, preservative, pigment, vitamin, active agent, emulsifier, UV filter, sunscreen, surfactant, thermal water, flower water, liposome, cyclodextrin, perfume, humectant, glycol, vegetable oil, vegetable butter, natural or synthetic wax, silicone, chelating agent, antioxidant, sugar or combinations thereof.

21. A method for preparing a cosmetic or dermatologic compositions comprising:
   adding a composition according to claim 1 to dermatologic or cosmetic component(s) and
   recovering the cosmetic or dermatologic composition obtained.

22. A method for preparing the composition of claim 1 comprising-mixing sclerotium gum, xanthan gum and pullulan so as to obtain a powder, and optionally compacted the powder into bars or granules.

* * * * *